United States Patent [19]
Lui

[11] Patent Number: 5,261,885
[45] Date of Patent: Nov. 16, 1993

[54] VALVED CATHETER

[75] Inventor: Chun K. Lui, Monroeville, Pa.

[73] Assignee: Cook Pacemaker Corporation, Leechburg, Pa.

[21] Appl. No.: 913,243

[22] Filed: Jul. 14, 1992

[51] Int. Cl.⁵ .................. A61M 25/00; F16K 15/14
[52] U.S. Cl. ............................. 604/247; 604/266; 604/280; 137/845
[58] Field of Search ............... 604/52, 53, 118, 246, 604/247, 256, 264, 266, 280; 137/843, 845

[56] References Cited

U.S. PATENT DOCUMENTS

| | | | |
|---|---|---|---|
| 3,885,561 | 5/1975 | Cami. | |
| 3,888,249 | 6/1975 | Spencer | 604/247 |
| 4,003,398 | 1/1977 | Duveau | 137/512 |
| 4,240,434 | 12/1980 | Newkirk | 604/247 X |
| 4,549,879 | 10/1985 | Groshong et al. | 604/247 |
| 4,657,536 | 4/1987 | Dorman | 604/247 |
| 4,671,796 | 6/1987 | Groshong et al. | 604/247 |
| 4,701,166 | 10/1987 | Groshong et al. | 604/247 |
| 5,030,210 | 7/1991 | Alchas | 604/247 |
| 5,112,301 | 5/1992 | Fenton, Jr. et al. | 604/30 |
| 5,147,332 | 9/1992 | Moorehead | 604/247 |
| 5,160,325 | 11/1992 | Nichols et al. | 604/247 |
| 5,163,921 | 11/1992 | Feiring | 604/247 |
| 5,190,524 | 3/1993 | Wex | 604/80 |

Primary Examiner—John D. Yasko
Assistant Examiner—Adam J. Cermak
Attorney, Agent, or Firm—Richard J. Godlewski

[57] ABSTRACT

A closed-end catheter having a flat-surfaced valve positioned in a recess about the distal portion of the catheter for preventing retrograde flow of blood therethrough when positioned in a blood vessel of a patient. The valve catheter comprises a flexible material, cylindrical tube having a U-shaped outer wall extending longitudinally about the distal portion thereof. A flat-surfaced valve is positioned in the recess along the U-shaped distal portion and attached to the outer wall. The valve is formed by inserting a flat-surfaced rod in the U-shaped portion of the tube to stretch the outer wall. A flat-surfaced layer of flexible material is applied over the flat-surfaced rod to the stretched outer wall. The flexible material layer is cured and a longitudinal fluid aperture formed therein with the rod remaining in the passage of the U-shaped portion. The rod is then removed and a plug inserted into the passage to close the distal end of the catheter. The stretched outer wall of the U-shaped portion compresses the fluid aperture to a predetermined closed position to prevent fluid leakage therethrough.

20 Claims, 2 Drawing Sheets

VALVED CATHETER

TECHNICAL FIELD

This invention relates generally to medical devices such as catheters and, in particular, to catheters with fluid valves.

BACKGROUND OF THE INVENTION

Catheters are often positioned in the vascular system of a patient for long-term drug infusion or fluid aspiration. A problem with leaving a catheter positioned in the vascular system of a patient for a long duration is that thrombosis occurs at the distal end of the catheter lumen where there is even a small amount of retrograde blood flow into the catheter. In the vascular system, blood clots form quickly and thrombosis obstructs a catheter lumen over time. A thrombotic obstruction makes the catheter lumen useless and creates a risk for the patient. If a catheter lumen is only partially obstructed by thrombosis and fluid is injected therethrough, a thrombus is flushed loose from the catheter lumen and flows through the vascular system to a narrow diameter site. As a result, the loose thrombus potentially causes an undesirable obstruction in a small or narrowed vessel of the vascular system. If the thrombus obstructs a small vessel in the lung, heart, or brain, serious complications such as pulmonary embolism, heart attack, or stroke may result.

One approach to preventing retrograde fluid flow into a catheter lumen is the use of a catheter having sufficient rigidity for introduction into tissue to provide epidural anesthesia. The rigid catheter includes several longitudinal slits in the catheter wall about the distal end thereof. A limitation of this rigid catheter is that it is not flexible or pliable for atraumatic introduction through the tortuous vessels of the vascular system.

Another approach to preventing the retrograde blood flow that causes thrombosis is the use of a closed end, silicone catheter with a single, linearly extending, two-way slit valve near the distal end thereof. The slit valve is contiguous with the silicone rubber catheter wall, which is treated with dimethylsiloxane for weakening the wall adjacent the valve. A problem with the use of this slit valve is that the valve is positioned on the circumference of the catheter wall. The sides of the slit valve are inadequately supported by the adjacent, curved catheter wall. The inadequately supported sides of the slit valve fail to form a watertight seal and, as a result, permit leakage. Another problem with the use of this slit valved catheter is that the catheter wall adjacent the valve is weakened by dimethylsiloxane, which further decreases support for the slit valve. As a result, the valve is susceptible to improper or crooked closure and retrograde blood leakage. Furthermore, the weakened catheter wall makes the slit valve more fragile and susceptible to damage in repeated operation. In addition, the weakened wall potentially causes collapse of the slit valve against the opposite inner wall of the catheter, thereby preventing use of the valve for aspiration.

Yet another problem with the use of this silicone, slit valved catheter is that the catheter has a smooth exterior surface without a traverse protrusion. As a result, the slit valve is positioned on the circumferential periphery of the catheter adjacent or possibly abutting a blood vessel wall. During irrigation, fluid flow is flushed out of the slit valve and directly against the intimal layer of the blood vessel wall. This fluid flow deflects off the blood vessel wall and creates turbulence in the blood vessel lumen, thereby loosening particles of plaque and other deposits from the blood vessel wall. The loosened particles flow through the vascular system and present the risk of obstructing a small or partially occluded blood vessel. As previously discussed, undesirable obstructions can cause pulmonary embolism, heart attack, or stroke in a patient. During aspiration, the blood vessel wall is potentially drawn against and possibly into the slit valve. As a result, the blood vessel wall can be traumatized and damaged, which causes thrombosis and other cell proliferation and deposition to occur and subsequently obstruct the catheter or blood vessel. Again, trauma to the blood vessel wall loosens plaque and other deposits therefrom and presents the risk of undesirable obstructions as previously discussed.

Yet another problem with this catheter is that the size of the catheter and the durometer of the catheter material must be designed to meet the needs of a particular valve design. This significantly limits the inside and outside diameters of the catheter along with the wall thickness. The durometer of the catheter material can be utilized to change the dimensions of the catheter to meet a particular valve design; however, the range of catheter dimensions and material durometer is still limited.

SUMMARY OF THE INVENTION

The foregoing problems are solved and a technical advance is achieved in an illustrative closed-end catheter having a valve positioned in a recess about the distal portion of the catheter. The valve includes a fluid aperture that communicates with the exterior of the catheter and a longitudinal passage within the catheter. The outer wall of the catheter about the distal portion thereof advantageously compresses the fluid aperture to a closed position for preventing retrograde blood flow and thrombosis about the distal end of the catheter when positioned in a blood vessel of a patient.

The valved catheter comprises an elongated member such as a flexible material, cylindrical tube having a distal portion, an outer wall, and a passage extending longitudinally therein. The recess is formed in the outer wall extending longitudinally along the distal portion of the elongated member. The valve is positioned in the recess of the elongated member and attached to the outer wall about the distal portion. The flat-surfaced valve is formed by positioning in the passage along the distal portion a rod having a flat surface extending longitudinally therealong. The rod laterally stretches the outer wall along the distal portion. To form the valve, a flat-surfaced layer of flexible material is attached over the flat-surfaced rod to the stretched outer wall along the distal portion. The fluid aperture is formed by placing a longitudinal slit in the layer of flexible material with the rod in the passage. The rod is subsequently removed, and a plug is inserted in the passage to close the distal end of the catheter. The laterally stretched outer wall along the distal portion now advantageously compresses the fluid aperture to a predetermined closed position for preventing fluid leakage therethrough.

The fluid aperture comprises a longitudinal slit formed through the flat-surfaced layer of flexible material that communicates exterior to and with the passage of the elongated member.

The distal portion of the outer wall is substantially U-shaped and compresses the slit to the closed position for advantageously preventing fluid flow therethrough. The flat-surfaced layer of the flexible material is longitudinally attached to the U-shaped outer wall. The closed distal end of the catheter includes a plug that is positioned in and closes the distal end of the passage of the elongated member tube.

DETAILED DESCRIPTION

Figure 1:
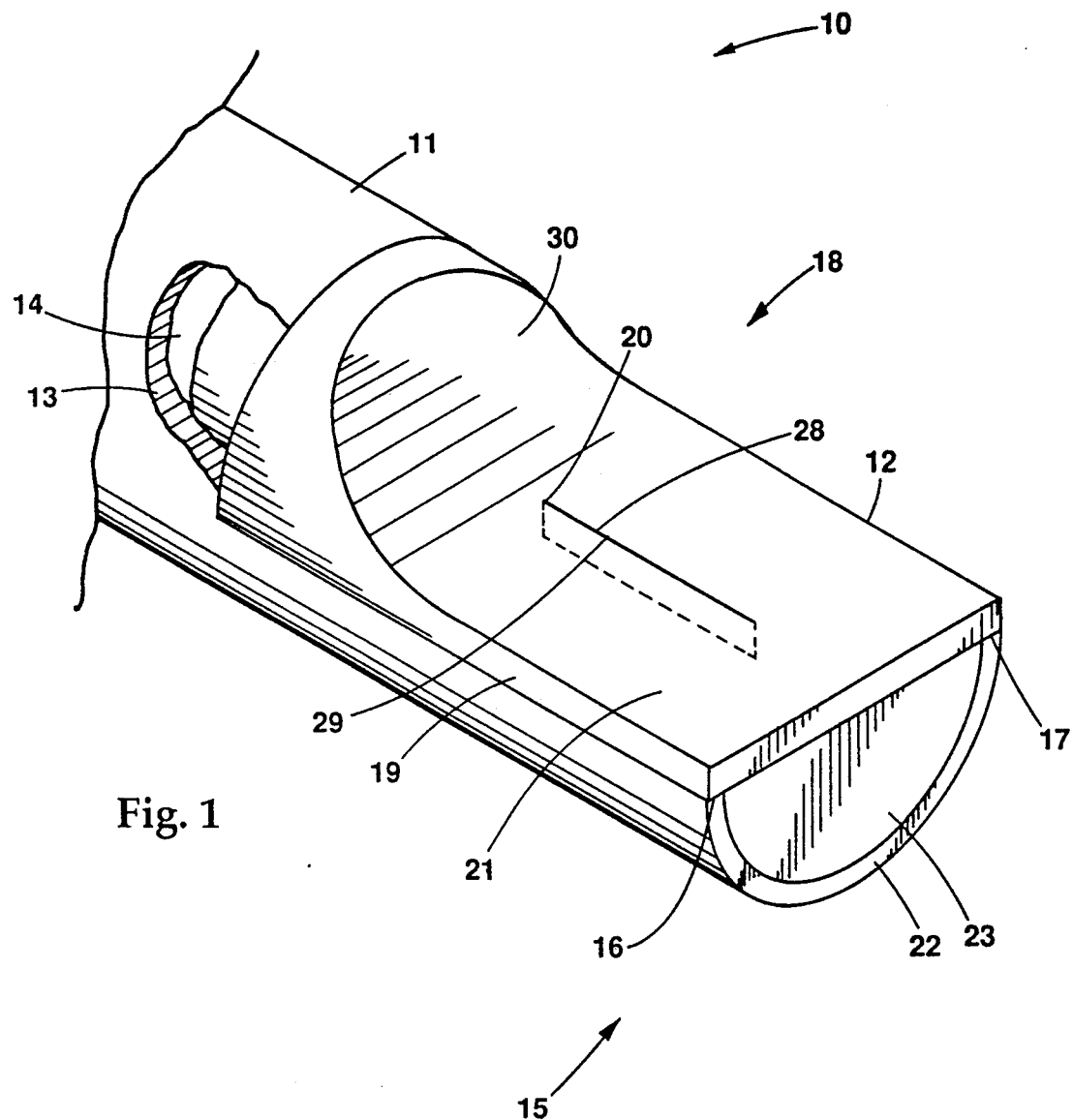
FIG. 1 depicts a pictorial view of a distal end segment of an illustrative valved catheter of the present invention.

Depicted in FIG. 1 is a pictorial view of the distal end segment of illustrative valved catheter 10 comprising elongated member tube 11 and valve 12 with compressed, closed fluid aperture 20 positioned about the distal end thereof. The proximal end (not shown) of the valved catheter is connected, for example, to a commercially available implantable port or a connector fitting for the injection or aspiration of fluids such as medicants, blood, and the like. When the valved catheter is positioned in a blood vessel of a patient, the fluid aperture prevents retrograde blood flow and thrombosis about the distal end of the catheter. The valved catheter further comprises closed distal end 22 formed by plug 23 for preventing longitudinal fluid flow from the catheter.

Elongated member tube 11 includes outer wall 13 and passage 14 extending longitudinally therethrough. Elongated member tube 11 further includes longitudinal recess 18 for forming U-shaped distal portion 15 with ends 16 and 17 positioned at the top of the two sides of the U-shaped portion. Recess 18 and U-shaped distal portion 15 provide for the attachment of valve 12 to the elongated member tube. Elongated member tube 11 is a flexible material cylindrical tube comprising, for example, commercially available 1.6 mm silicone material tubing with an outside diameter of approximately 125", an inside diameter of approximately 0.062", and a length of approximately 70 cm. The silicone material of elongated member tube 11 has a durometer of approximately 65 on the Shore A scale. Recess 18 is, for example, approximately 0.061±0.002" in height and 0.515±0.017" in length extending proximally from the distal end of the elongated member tube.

Valve 12 comprises flexible material layer 19 with slit or fluid aperture 20 positioned in flat surface 21 of the flexible material layer. The fluid aperture provides for the flow of fluid between passage 14 and the exterior of the valved catheter. Flat surface 21 of the flexible material layer provides for both sides of the fluid aperture to present squarely abutting surfaces 28 and 29 when valved catheter 10 is at rest and the fluid aperture is compressed closed. Flexible material layer 19 is attached to outer wall 13 of the elongated member longitudinally along ends 16 and 17 of the U-shaped distal portion. The width of the flexible material layer (0.130") is greater than the outside diameter (0.125") of the portion of the elongated member where the flexible material layer is attached at ends 16 and 17. When the valved catheter is at rest, the U-shaped ends 16 and 17 of the elongated member tube compress the flexible material layer for forcing the slit or fluid aperture to a closed position, thereby preventing fluid leakage or retrograde blood flow. When the valved catheter is in use, the force of fluid being injected or withdrawn through passage 14 causes abutting slit surfaces 28 and 29 to laterally stretch, thereby permitting flow through fluid aperture 20. Flexible material layer 19 comprises a material with a desirable durometer and a curing mechanism that is similar to that of the silicone tubing material of elongated member 11. Flexible material layer 19 preferably comprises, for example, a silicone material such as Silastic Q7-4850 commercially available from Dow Corning, Midland, Mich. This Silastic Q7-4850 material has a durometer of approximately 50 on the Shore A scale. Flexible material layer 19 is, for example, approximately 0.015+0.000" and −0.005" thick, 0.500±0.015" long, and 130" wide, with a radius of approximately 0.050±0.010" at proximal, upper curved portion 30 thereof for providing flat surface area 21, which extends from the curved portion to the distal end of the elongated member tube. Although the radius in the flexible material layer does not affect valve function, sharp corners on the catheter are preferably avoided and rounded off as needed for facilitating atraumatic introduction of the valved catheter into the vessels of the vascular system of a patient. Fluid aperture 20 is, for example, a slit approximately 0.236±0.015" in length and extends longitudinally along the flat surface area of the flexible material layer beginning 0.157±0.015" from the proximal end of the flexible material layer. Plug 23 comprises, for example, the same material as the flexible material layer, which is classified as a liquid silicone and is injected into the passage of the elongated member tube and then heated and cured for forming the closed distal end of the elongated member tube.

Ten valved catheters identical to the above-described valved catheter 10 were immersed in a 37° C. solution having the same viscosity of blood for simulating in vivo conditions. A Vital-Port ®reservoir, commercially available from Cook Pacemaker Corporation, Leechburg, Pa., was attached to each catheter. A 20 gauge needle with syringe was inserted in the port septum for repeated cycles of injection and withdrawal through the valved catheter. The syringe was driven by an air cylinder which was set to inject and withdraw 10 cc for each stroke of the syringe. The duration of each cycle was 30 seconds. Each of the tested valved catheters underwent 2500 cycles of injection/withdrawal. The valve-opening pressures for injection and withdrawal were measured at the beginning of the test and every 500 cycles thereafter.

Pressures recorded prior to testing and at 500 cycle intervals through 2500 cycles exhibited average injection pressures ranging from 0.3 to 0.7 psi. Average withdrawal pressures recorded at the same intervals ranged from 2.3 to 3.2 psi. Visual inspection of the catheter valves showed no damage through the test, indicating valve integrity was maintained. Throughout testing, positive and negative pressures were required to open the valve for injection and withdrawal, respectively, indicating the valve functioned properly by remaining closed unless subjected to a differential pressure.

Alternatively, the compression force imposed on the fluid aperture is varied by using different materials for the flexible material layer or elongated member tube or by modifying the durometer of the materials used, the dimensions of the flexible material layer, or the relative inner and outer diameters of the elongated member tube and distal portion thereof. However, a valve can be attached to virtually any size and durometer elongated member tube.

Figure 2:
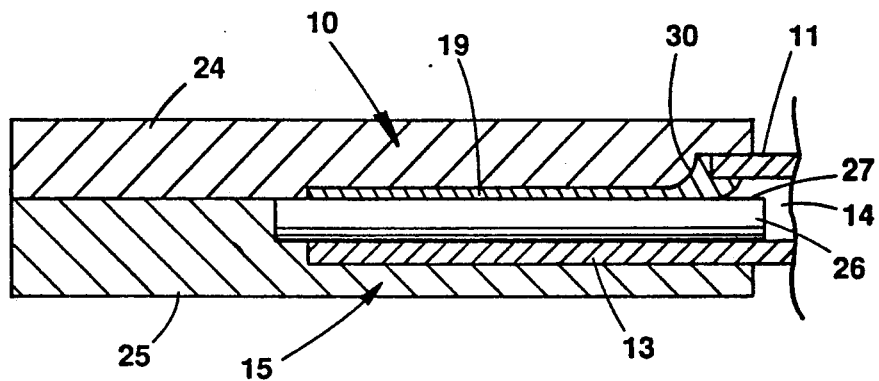
FIGS. 2-4 depict an illustrative method of forming the valved catheter of FIG. 1.
Figure 3:
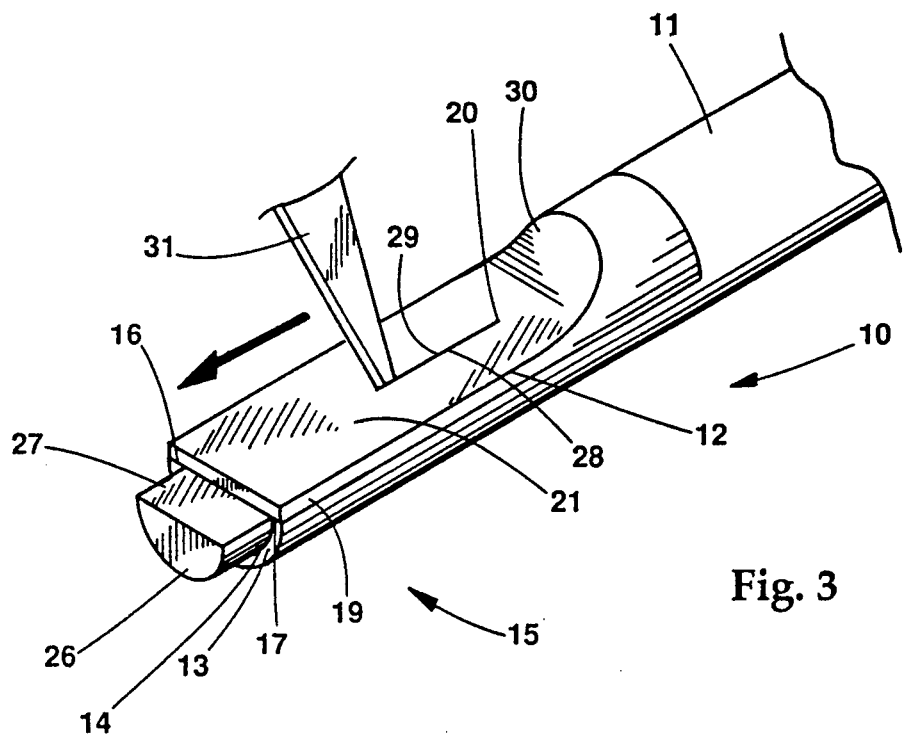
Figure 4:
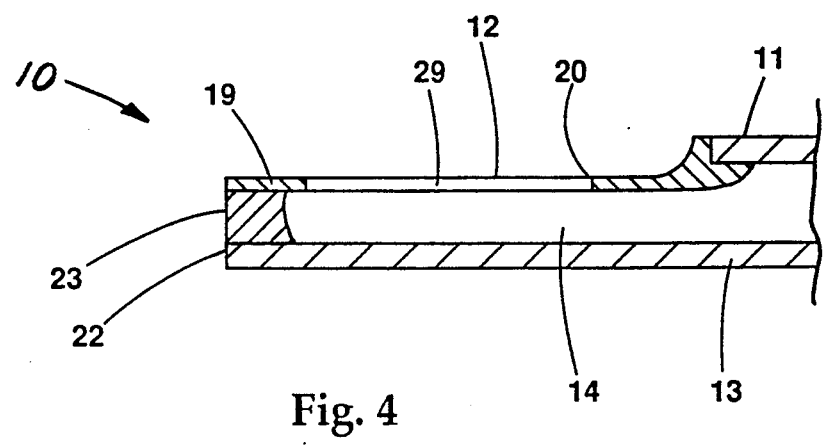

A preferred method of forming illustrative valved catheter 10 is depicted in FIGS. 2-4. FIG. 2 depicts a cross-sectioned longitudinal view of elongated member tube 11 positioned between well-known mold halves 24 and 25 with flat-surfaced pin or rod 26 positioned in passage 14 of the elongated member tube. Rod 26 is a round, metal hardened pin such as a gauge pin or drill blank that has been ground down for forming flat surface 27 (shown in FIG. 3) extending longitudinally therealong. Rod 26 has, for example, a maximum outside diameter of 0.067" and a crossexample sectional height of 0.033". Elongated member tube 11 has been cut longitudinally in outer wall 13 to form recessed, U-shaped distal portion 15. Since elongated member tube 11 has a passage with an inside diameter of 0.062", rod 26 positioned in the passage laterally stretches the outer wall of the elongated member tube to an inside diameter of 0.067" and an outside diameter of 0.130". Flexible material layer 19 is applied over the flat surface of the rod and over the laterally stretched, U-shaped outer wall of distal portion 15 of the elongated member. The elongated member tube with flexible material layer positioned over the laterally stretched distal portion thereof and the rod positioned in the passage are heated for fixedly attaching the flexible material layer to the elongated member tube and curing the materials.

FIG. 3 depicts a pictorial view of elongated member tube 11 and flexible material layer 19 fixedly attached with rod 26 positioned in passage 14 and removed from the mold halves shown in FIG. 2. Flat surface 21 of the flexible material layer is cut longitudinally using knife 31 to form slit or fluid aperture 20. When the slit is being cut, rod 26 with flat surface 27 remains in passage 14 for laterally stretching ends 16 and 17 of outer wall 13 about distal U-shaped portion 15.

FIG. 4 depicts a cross-sectioned longitudinal view of the valved catheter with the rod removed from passage 14 and a plug 23 positioned at distal end 22 of the elongated member tube for providing a closed distal end. The plug is affixed to elongated member tube 11 and flexible material layer 19 by injecting material into the distal end of passage 14 and then heating and curing the material. When the rod is removed from the passage of the elongated member, the U-shaped ends of outer wall 13 want to return to an inside diameter of 0.062" and an outside diameter of 0.125" and, as a result, compress flexible material layer 19 and forcibly close fluid aperture 20.

It is to be understood that the above-described valved catheter is merely an illustrative embodiment of the principles of this invention and that other valved catheters may be devised by those skilled in the art without departing from the spirit and scope of this invention. It is contemplated that this valve can be utilized on catheters used in other regions of the body besides the vascular system. It is further contemplated that a catheter, particularly a multi-lumen catheter, can include more than one of the above-described valves. It is also further contemplated that the fluid aperture can be oriented in another direction, such as transverse or diagonal with respect to the axis of the elongated member tube. For example, if the fluid aperture is oriented transversely in the above-described illustrative valved catheter, the fluid aperture is biased open when the catheter is at rest and forced closed by fluid flow in the elongated member tube passage. This embodiment of the valved catheter is contemplated for a clinical application wherein a biased open valve is desirable. The opening and closing pressures of the valve can be varied depending on the durometer and thickness of the valve layer material along with varying the dimensions and durometer of the elongated member tube.

What is claimed is:

1. A valved catheter comprising:
   an elongated member having a distal portion, an outer wall, a passage extending longitudinally therein, and a recess in said outer wall extending longitudinally along said distal portion; and
   a valve positioned in said recess, attached to said outer wall about said distal portion and having a fluid aperture communicating exterior to and with said passage of said member, said outer wall about said distal portion compressing said fluid aperture to a predetermined position.

2. The catheter of claim 1 wherein said valve comprises a flat-surfaced layer of flexible material and wherein said fluid aperture comprises a slit formed through said flat-surfaced layer of flexible material and communicating exterior to and with said passage of said member.

3. The catheter of claim 2 wherein said outer wall along said distal portion is substantially U-shaped and compresses said slit to said predetermined position.

4. The catheter of claim 3 wherein said flat-surfaced layer of flexible material is longitudinally attached to the ends of said U-shaped outer wall.

5. The catheter of claim 1 wherein said member further comprises a closed distal end.

6. The catheter of claim 5 wherein said closed distal end includes a plug positioned in and closing a distal end of said passage of said member.

7. The catheter of claim 1 wherein said valve is formed by positioning in said passage along said distal portion a rod having a flat surface extending longitudinally therealong, said rod when in said passage laterally stretching said outer wall along said distal portion.

8. The catheter of claim 7 wherein said valve is further formed by applying a layer of flexible material over said flat surface of said rod when in said passage and attaching said layer to said outer wall along said distal portion.

9. The catheter of claim 8 wherein said aperture is formed by placing a longitudinal slit in said layer of flexible material when said rod is in said passage.

10. The catheter of claim 9 wherein said catheter is further formed by inserting a plug in and closing a distal end of said passage of said member when said rod is removed from said passage.

11. The catheter of claim 1 wherein said predetermined position of said aperture is a closed position.

12. A valved catheter comprising:
   a flexible material, cylindrical tube having an outer wall, a closed distal end and a passage extending longitudinally therein, said outer wall having a U-shaped portion extending proximally from said closed distal end for a predetermined distance;
   a valve communicating exterior to and with said passage of said tube and having a flat-surfaced layer of a flexible material attached longitudinally to said U-shaped portion of said outer wall, said U-shaped portion of said outer wall being laterally stretched when said layer of flexible material is attached thereto.

13. The catheter of claim 12 wherein said valve includes a slit formed through said flat-surfaced layer of said flexible material and communicating exterior to and with said passage of said tube.

14. The catheter of claim 13 wherein said closed distal end includes a plug positioned in and closing said passage of said tube.

15. The catheter of claim 12 wherein said valve is formed by positioning in said passage against said U-shaped outer wall a rod having a flat surface extending longitudinally therealong.

16. The catheter of claim 15 wherein said flat-surfaced layer of said flexible material is formed by applying a layer of said flexible material over said flat surface of said rod when in said passage against said U-shaped outer wall and attaching said layer of said flexible material to said U-shaped outer wall.

17. The catheter of claim 16 wherein said valve is further formed by placing a longitudinal slit in said flat-surfaced layer of said flexible material when said rod is in said passage.

18. The catheter of claim 12 wherein said U-shaped wall is formed by longitudinally cutting away a portion of said outer wall about said distal end.

19. The catheter of claim 17 further comprising a plug positioned in and closing said passage when said rod is removed from said passage.

20. A valved catheter comprising:

a flexible material, cylindrical tube having an outer wall, a distal end and a passage extending longitudinally therein, said outer wall having a U-shaped portion extending proximally from said distal end for a predetermined distance;

a valve having a layer of a flexible material attached to said U-shaped portion of said outer wall, said layer having a flat surface and a slit formed in said flat surface and through said layer communicating exterior to and with said passage of said tube, said valve being formed by positioning in said passage against said U-shaped portion of said outer wall a rod having a flat surface extending longitudinally therealong, said rod laterally stretching said U-shaped portion of said outer wall, applying said layer of said flexible material over said flat surface of said rod when in said passage, attaching said layer of said flexible material to said U-shaped portion of said outer wall, and placing a longitudinal slit in said layer of said flexible material when said rod is in said passage, said U-shaped portion of said outer wall being formed by longitudinally cutting away a portion of said tube about said distal end; and a plug positioned in and closing said distal end of said passage when said rod is removed from said passage.

* * * * *